(12) United States Patent
de Juan, Jr. et al.

(10) Patent No.: US 8,535,333 B2
(45) Date of Patent: Sep. 17, 2013

(54) OCULAR IMPLANT APPLIER AND METHODS OF USE

(75) Inventors: Eugene de Juan, Jr., San Francisco, CA (US); Steven John, Fremont, CA (US); Jose Garcia, Fremont, CA (US); Richard S. Lilly, San Jose, CA (US); Thomas A. Silvestrini, Alamo, CA (US)

(73) Assignee: Transcend Medical, Inc., Menlo Park, CA (US)

( * ) Notice: Subject to any disclaimer, the term of this patent is extended or adjusted under 35 U.S.C. 154(b) by 338 days.

(21) Appl. No.: 12/846,201

(22) Filed: Jul. 29, 2010

(65) Prior Publication Data

US 2011/0112546 A1     May 12, 2011

Related U.S. Application Data

(60) Provisional application No. 61/229,660, filed on Jul. 29, 2009, provisional application No. 61/353,139, filed on Jun. 9, 2010.

(51) Int. Cl.
*A61F 11/00*     (2006.01)

(52) U.S. Cl.
USPC .......................................... 606/108

(58) Field of Classification Search
USPC ................ 606/107, 161, 166, 108; 623/6.12, 623/23.64, 23.7; 604/8
See application file for complete search history.

(56) References Cited

U.S. PATENT DOCUMENTS

| 2007/0191863 A1 | 8/2007 | De Juan, Jr. et al. |
| 2008/0228127 A1* | 9/2008 | Burns et al. ....................... 604/9 |
| 2009/0182421 A1 | 7/2009 | Silvestrini et al. |
| 2010/0280317 A1 | 11/2010 | Silvestrini et al. |

* cited by examiner

*Primary Examiner* — Thomas McEvoy
(74) *Attorney, Agent, or Firm* — Fred C. Hernandez; Mintz Levin Cohn Ferris Glovsky and Popeo, P.C.

(57) ABSTRACT

Described herein is a delivery device and methods for delivering an ocular implant into an eye. The delivery device includes a proximal handle portion; a distal delivery portion coupled to a distal end of the handle portion and configured to releasably hold an ocular implant and includes a sheath positioned axially over a guidewire; and a metering system configured to provide visual guidance regarding depth of advancement of an implant positioned on the guidewire into an anatomic region of the eye. Also disclosed is a device and method for loading an implant onto the delivery device.

10 Claims, 16 Drawing Sheets

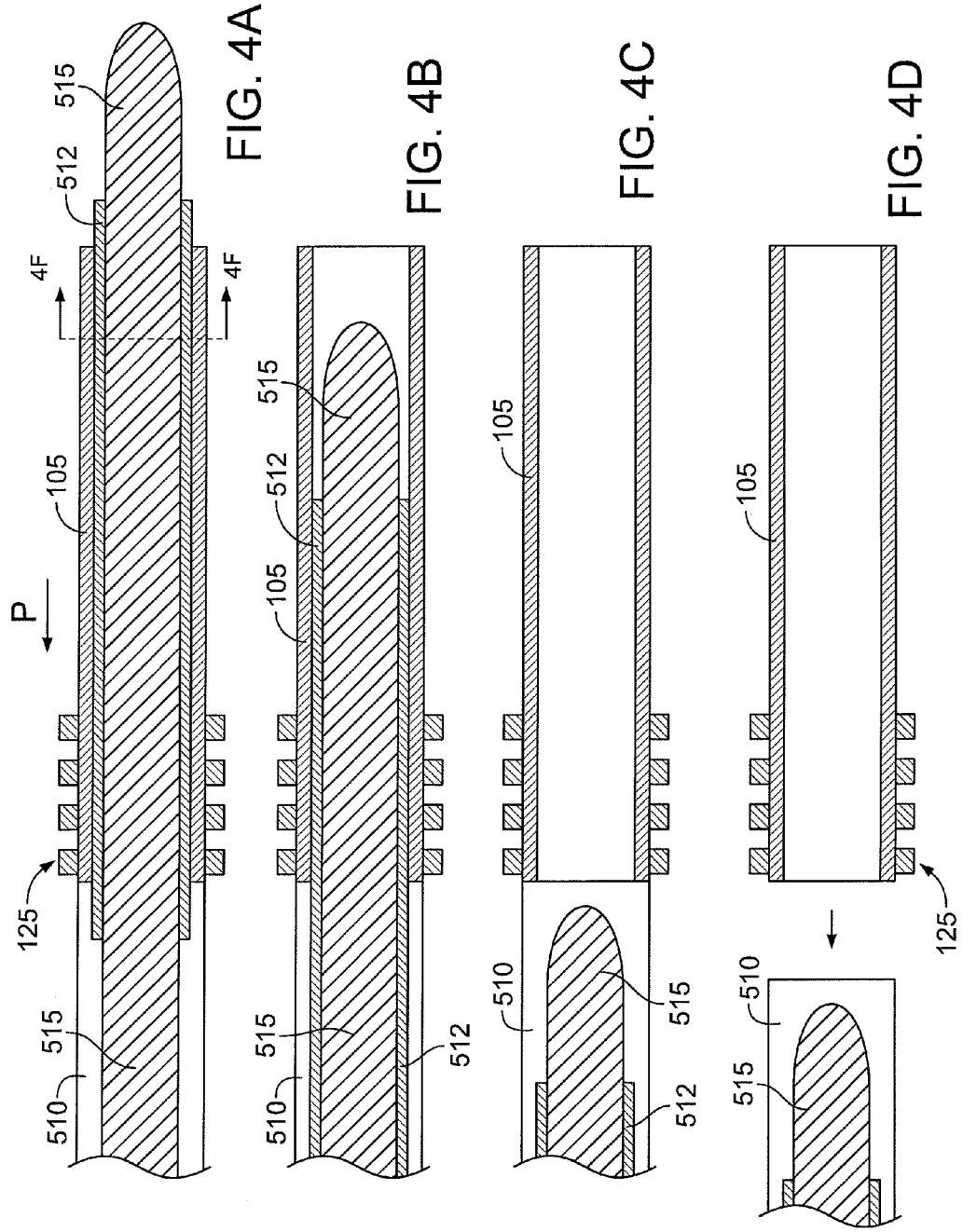

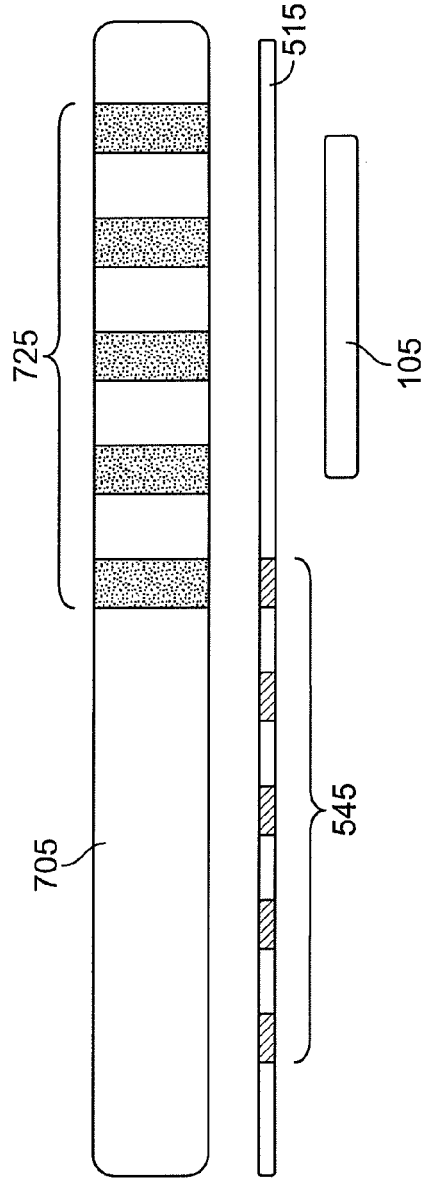
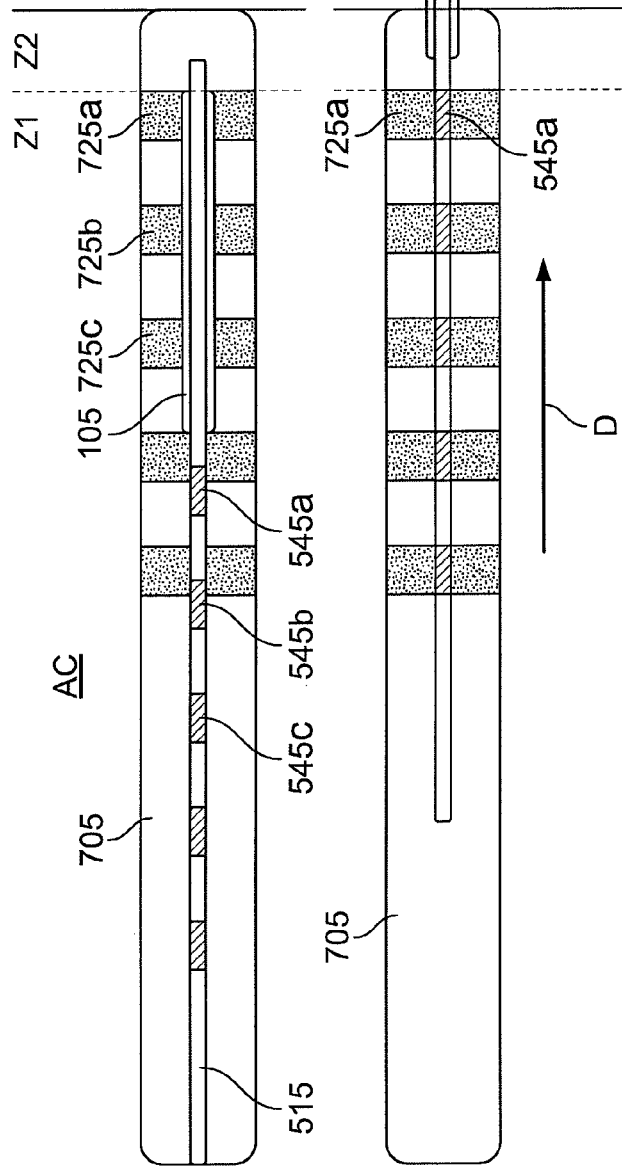
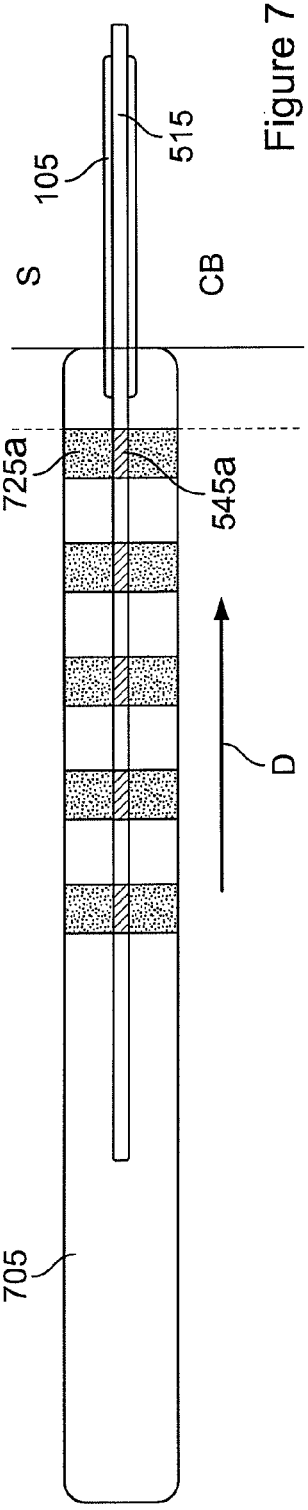
Figure 7A
Figure 7B
Figure 7C

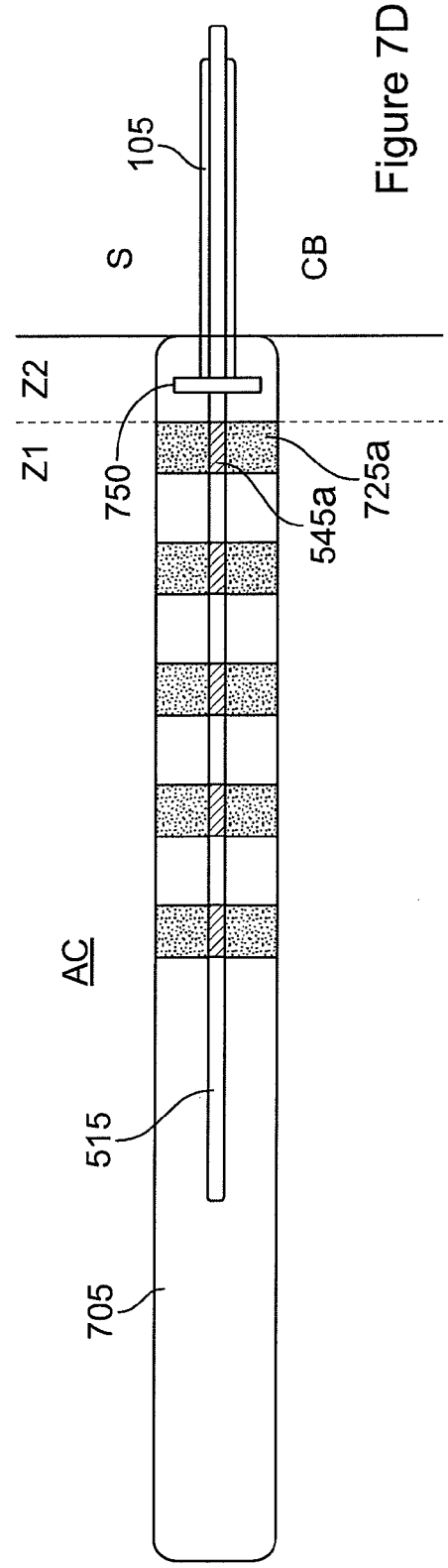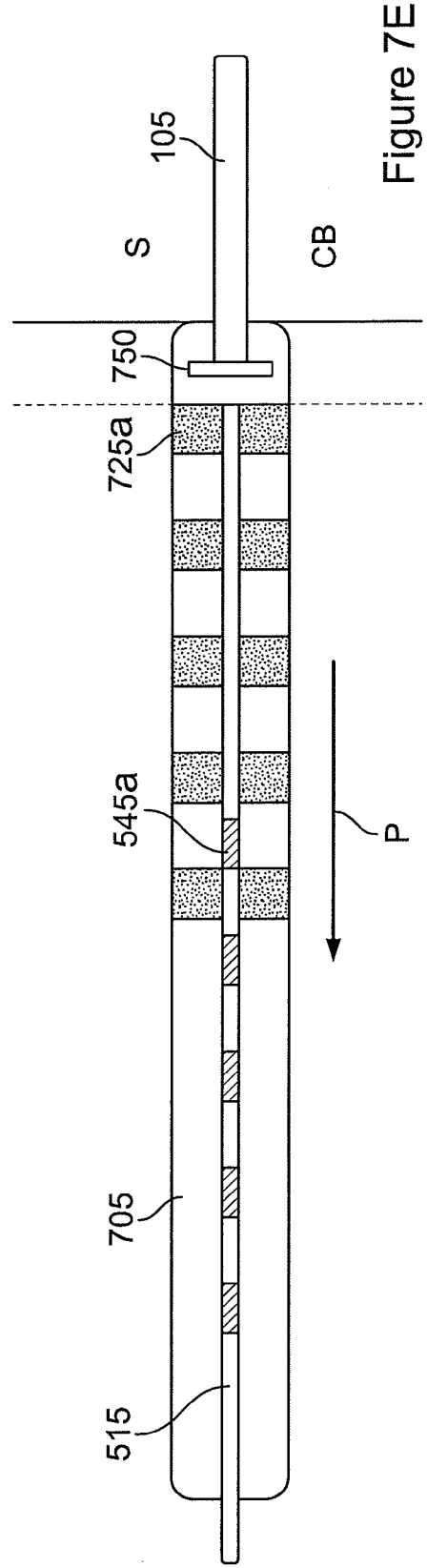

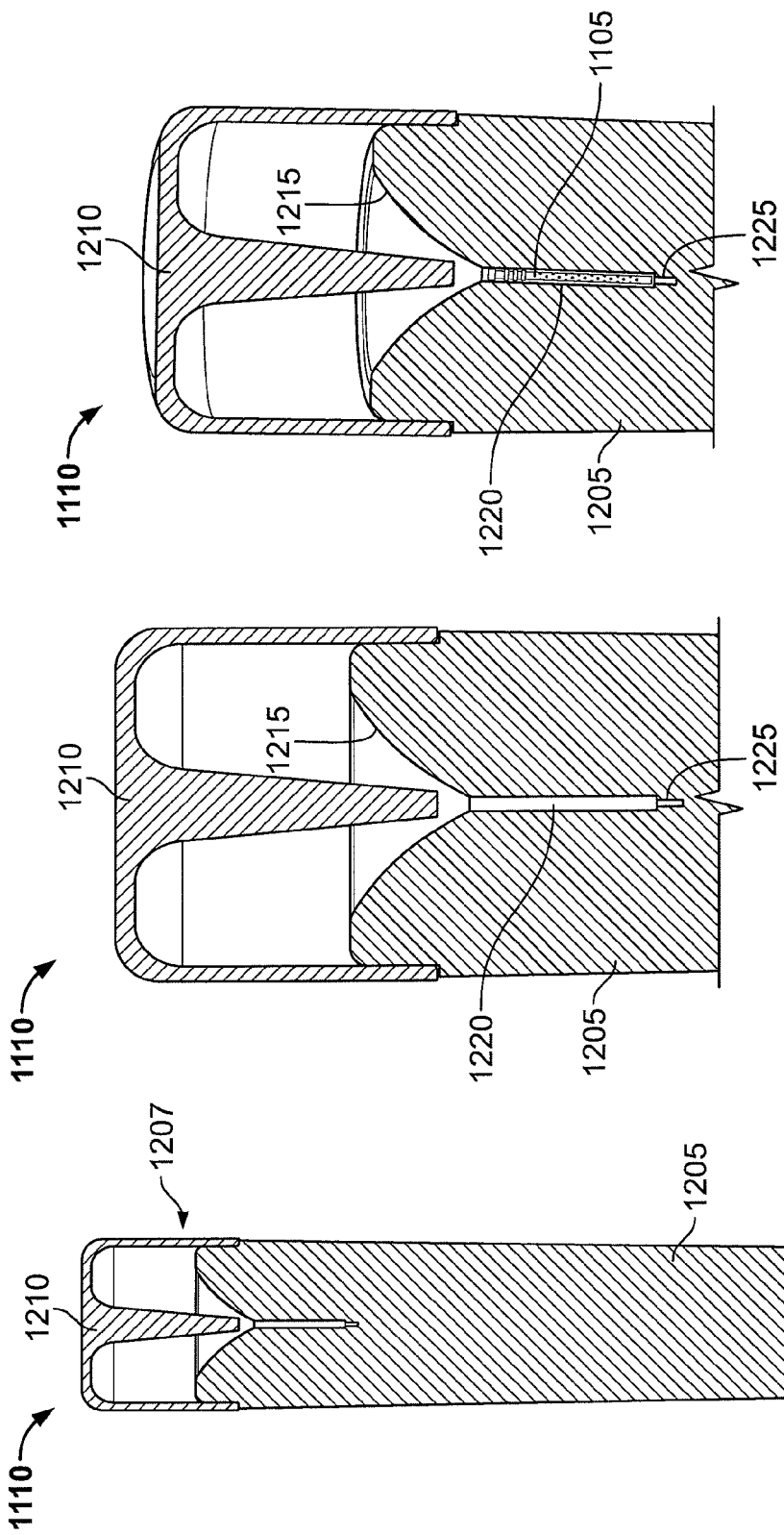

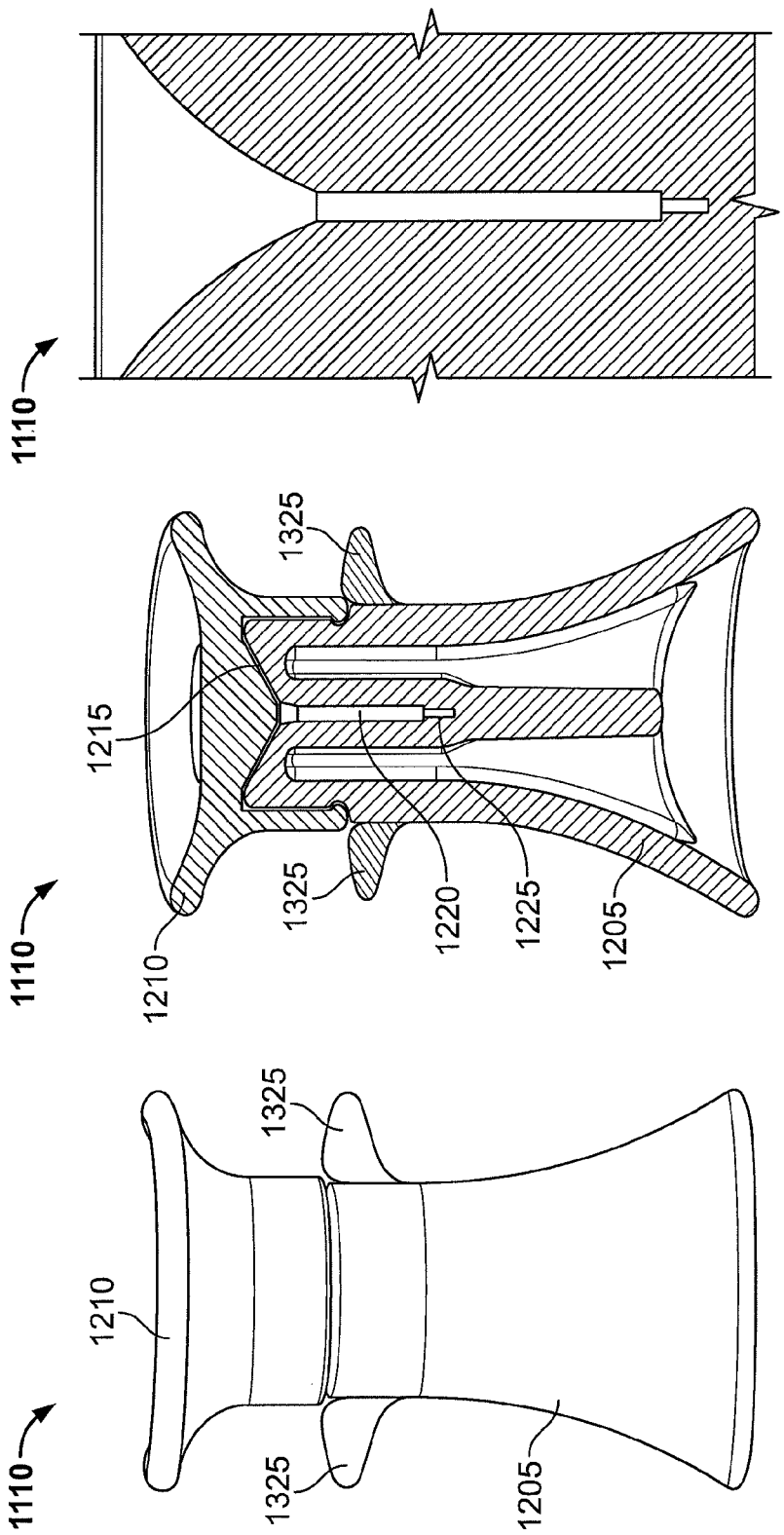

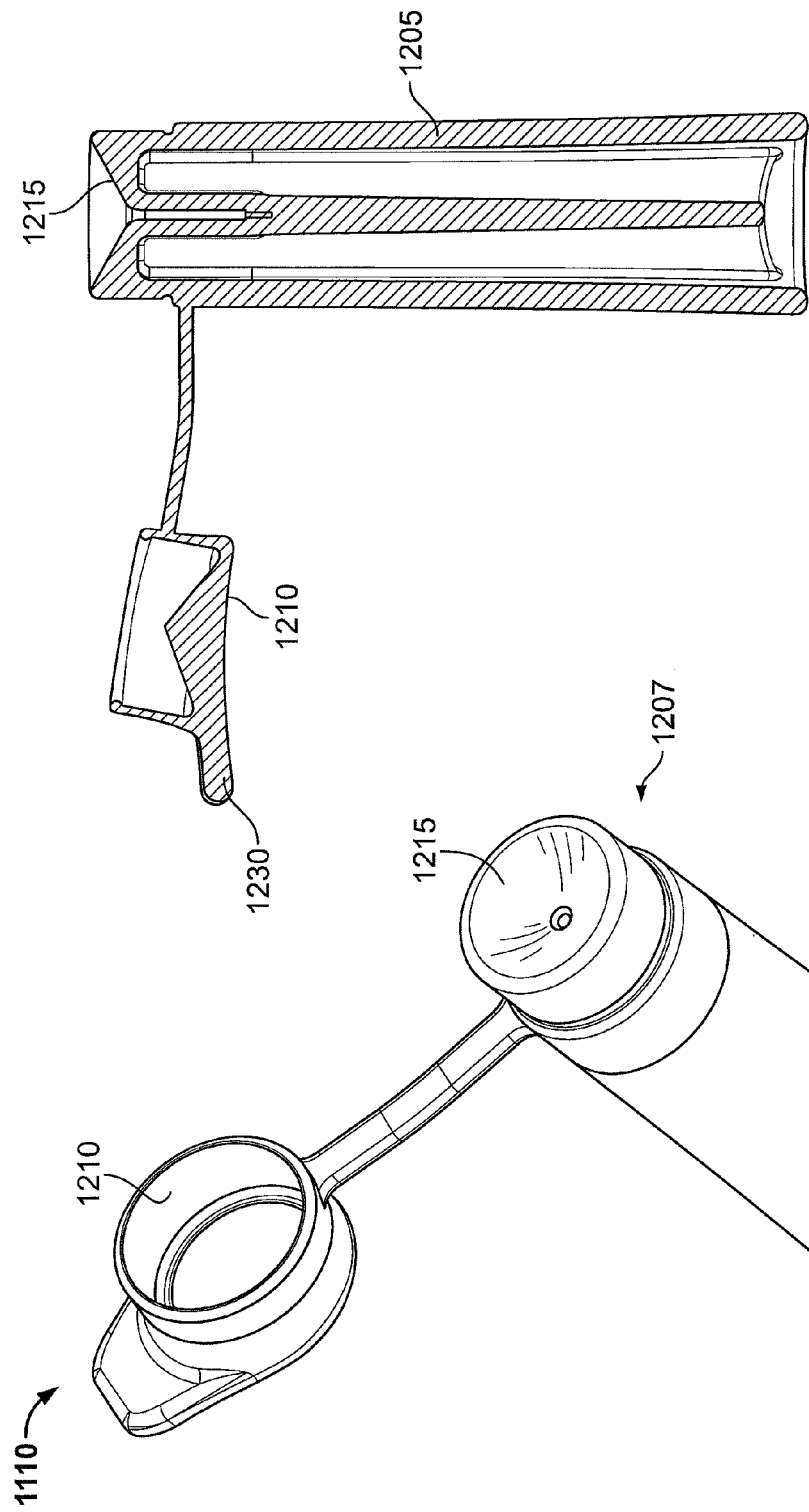

OCULAR IMPLANT APPLIER AND METHODS OF USE

REFERENCE TO PRIORITY DOCUMENT

This application claims priority of U.S. Provisional Patent Application Ser. Nos. 61/229,660, entitled "Ocular Implant Applier and Methods of Use", filed Jul. 29, 2009 and 61/353,139, entitled "Optical Implant Loading Device and System", filed Jun. 9, 2010. Priority of the filing dates of Jul. 29, 2009 and Jun. 9, 2010 is hereby claimed and the disclosures of the Provisional Patent Applications are hereby incorporated by reference.

BACKGROUND

This disclosure relates generally to methods and devices for use in delivering devices for treating glaucoma. The mechanisms that cause glaucoma are not completely known. It is known that glaucoma results in abnormally high pressure in the eye, which leads to optic nerve damage. Over time; the increased pressure can cause damage to the optic nerve, which can lead to blindness. Treatment strategies have focused on keeping the intraocular pressure down in order to preserve as much vision as possible over the remainder of the patient's life.

Past treatment includes the use of drugs that lower intraocular pressure through various mechanisms. The glaucoma drug market is an approximate two billion dollar market. The large market is mostly due to the fact that there are not any effective surgical alternatives that are long lasting and complication-free. Unfortunately, drug treatments need much improvement, as they can cause adverse side effects and often fail to adequately control intraocular pressure. Moreover, patients are often lackadaisical in following proper drug treatment regimens, resulting in a lack of compliance and further symptom progression.

With respect to surgical procedures, one way to treat glaucoma is to implant a drainage device in the eye. The drainage device functions to drain aqueous humor from the anterior chamber and thereby reduce the intraocular pressure. The drainage device is typically implanted using an invasive surgical procedure. Pursuant to one such procedure, a flap is surgically formed in the sclera. The flap is folded back to form a small cavity and the drainage device is inserted into the eye through the flap. Such a procedure can be quite traumatic as the implants are large and can result in various adverse events such as infections and scarring, leading to the need to re-operate.

Current devices and procedures for treating glaucoma have disadvantages and only moderate success rates. The procedures are very traumatic to the eye and also require highly accurate surgical skills, such as to properly place the drainage device in a proper location. In addition, the devices that drain fluid from the anterior chamber to a subconjunctival bleb beneath a scleral flap are prone to infection, and can occlude and cease working. This can require re-operation to remove the device and place another one, or can result in further surgeries.

Methods are known in the art for delivering an implant within the eye. Generally the methods include providing an elongate guidewire having at its distal region a piercing member intended to pass through tissues of the eye. The distal end of the guidewire is positioned within the lumen of the implant to be delivered and is advanced distally thereby piercing and/or bluntly dissecting tissues within the eye in order to deliver the implant to the target location. Delivery mechanisms intended to deliver the implant to a target depth and location of the eye can be bulky and require the procedure to be performed with minimal visual aide ("blind") or with a gonioscope.

SUMMARY

In view of the foregoing, there are herein disclosed devices and methods for use in delivering devices for treating glaucoma. In one aspect, there is disclosed a delivery device for delivering an ocular implant into an eye including a proximal handle portion; a distal delivery portion coupled to a distal end of the handle portion and configured to releasably hold an ocular implant. The delivery portion includes a sheath positioned axially over a guidewire. The delivery device also includes a metering system configured to provide visual guidance regarding depth of advancement of an implant positioned on the guidewire into an anatomic region of the eye. The anatomic region of the eye can be the suprachoroidal space.

The metering system can include a first series of graduated markings on the guidewire. The metering system can further include a second series of graduated markings on the sheath. The first series of graduated markings can correlate to the second series of graduated markings. The metering system can include one or more graduated markings on a surface of the distal delivery portion. The delivery system can further include an additional blank band distal to the one or more graduated markings. The metering system can include two or more unique bands of color.

The sheath can be in a fixed position relative to the handle portion and the delivery device can further include an elongate plate positioned adjacent the guidewire. The elongate plate can be adapted to move, protect, or deflect tissue during delivery of the implant into the eye. The elongate plate can further include one or more graduated markings.

In another aspect, there is disclosed a method of using a delivery system for implantation of a device into an eye including mounting an implant on a delivery device including a guidewire having a sheath coupled to the guidewire. The guidewire includes a first metering system at a distal end of the guidewire and the sheath includes a second metering system at a distal end of the sheath, the first and second metering systems having corresponding graduated markings. The method also includes inserting the implant on the delivery device into an anterior chamber through an incision in a cornea; advancing the implant on the delivery device through a transparent zone of the anterior chamber toward an opaque zone of the anterior chamber; seating a distal end of the guidewire at eye tissue where resistance is felt; reading through the transparent zone a first graduated marking of the first metering system, wherein the first graduated marking is aligned with an edge between the transparent zone and the opaque zone; advancing the implant on the guidewire into the eye tissue beyond where resistance is felt; and reading through the transparent zone a second graduated marking on the second metering system, wherein the second graduated marking is aligned with the edge between the transparent zone and the opaque zone.

The method can further include releasing the implant from the guidewire. The implant can provide a flow passageway between the anterior chamber and the suprachoroidal space. Inserting the implant can include inserting the entire implant into the anterior chamber. The first metering system can further include a blank band at the distal end region of the guidewire having a width. The width of the blank band can correspond to a width of the implant remaining within the anterior chamber once the implant is inserted into the eye tissue. The method can further include retaining the implant on the guidewire using a polymeric retention coating. Seating a distal end of the guidewire at eye tissue where resistance is felt can include seating the guidewire with a portion of the ciliary body having a tissue border with the scleral spur.

In another aspect, there is disclosed a method of implanting an ocular device into an eye including loading onto a delivery device a shunt having a proximal end, a distal end and a fluid passageway extending between the proximal end and the distal end; inserting the shunt loaded on the delivery device through an incision in a cornea and into an anterior chamber of the eye; passing the shunt from the anterior chamber past the scleral spur near the ciliary body of the eye into the suprachoroidal space; and positioning the shunt in a first position such that a first portion of the fluid passageway communicates with the anterior chamber and a second portion of the fluid passageway communicates with the suprachoroidal space to provide a fluid passageway between the suprachoroidal space and the anterior chamber.

Inserting the shunt through the incision can include passing the distal end of the shunt through the incision followed by the proximal end of the shunt. Passing the shunt from the anterior chamber past the scleral spur near the ciliary body of the eye into the suprachoroidal space can include dissecting a portion of the ciliary body away from a portion of scleral tissue. The distal end of the shunt can have a shape that is sufficiently blunt so as not to substantially penetrate the scleral spur or the portion of scleral tissue. Passing the shunt from the anterior chamber past the scleral spur near the ciliary body of the eye into the suprachoroidal space can include creating a puncture in the ciliary body and inserting the shunt through the puncture. Inserting the shunt through the puncture further can include passing the shunt through the puncture until a decrease in resistance to passage is sensed. Positioning the shunt in the first position can include substantially surrounding the shunt by eye tissue between the anterior chamber and the suprachoroidal space. Loading the shunt onto the delivery device can include inserting a distal end of the delivery device into a loading device. The loading device can have an atraumatic funnel that tapers into a cavity sized and configured to hold the shunt and a relief distal to the cavity sized and configured to accommodate the distal end of the delivery device and not the shunt. The distal end of the delivery device can include a metering system. The metering system can be configured to provide visual guidance regarding depth of advancement of the shunt positioned on the delivery device into an anatomic region of the eye.

Other features and advantages should be apparent from the following description of various embodiments, which illustrate, by way of example, the principles of the invention.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIGS. 4A-4D show an exemplary mechanism for delivering an implant.

FIG. 7A shows an exploded, top plan schematic view of another embodiment of a dual metering system and anatomical protector for delivering an implant.

FIGS. 7B-7E show top plan schematic views of the metering system and anatomical protector of FIG. 7A delivering an implant.

FIGS. 11A-11C illustrate an embodiment of a loading device;

FIGS. 12A-12C illustrate another embodiment of a loading device which incorporates ergonomic features;

FIGS. 13A-13B illustrate another embodiment of a loading device which incorporates a flip-cap;

It should be appreciated that the drawings herein are exemplary only and are not meant to be to scale.

DETAILED DESCRIPTION

There is a need for improved methods and devices for the treatment of eye diseases. In particular, there is a need for low profile, simplified delivery devices that can be used to deliver implants or other devices and possibly drugs and other therapeutic material into the eye for the treatment of glaucoma and other diseases. The delivery device described herein delivers an implant to a desired depth and location without the need for a viewing lens such as a goniolens.

Figure 1:
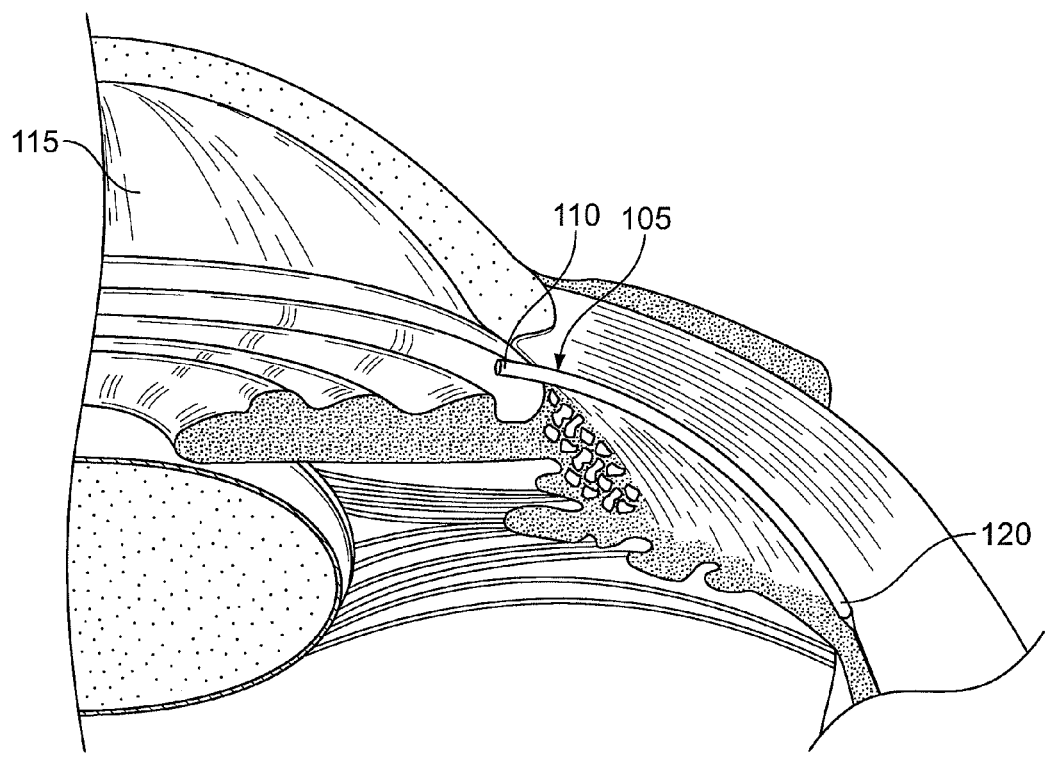
FIG. 1 is a cross-sectional, perspective view of a portion of the eye showing the anterior and posterior chambers of the eye.

FIG. 1 is a cross-sectional, perspective view of a portion of the eye showing the anterior and posterior chambers of the eye. A schematic representation of an implant 105 is positioned inside the eye such that a proximal end 110 is located in the anterior chamber 115 and a distal end 120 communicates with and/or is located in or near the suprachoroidal space (sometimes referred to as the perichoroidal space). The suprachoroidal space can include the region between the sclera and the choroid. The suprachoroidal space can also include the region between the sclera and the ciliary body or a portion thereof. In this regard, the region of the suprachoroidal space between the sclera and the ciliary body may sometimes be referred to as the supraciliary space. The implant described herein is not necessarily positioned between the choroid and the sclera. The implant may be positioned at least partially between the ciliary body and the sclera or it may be at least partially positioned between the sclera and the choroid. In any event, the implant provides a fluid pathway between the anterior chamber and the suprachoroidal space.

In an embodiment, the implant 105 is an elongate element having one or more internal lumens through which aqueous humor can flow from the anterior chamber 115 into the suprachoroidal space such as in the region between the sclera and the choroid. The implant 105 can have a substantially uniform internal diameter along its entire length, although the shape of the implant 105 can vary along its length (either before or after insertion of the implant), as described below. Moreover, the implant 105 can have various cross-sectional shapes (such as a, circular, oval or rectangular shape) and can vary in cross-sectional shape moving along its length. The cross-sectional shape can be selected to facilitate easy insertion into the eye. The following applications describe exemplary implants: U.S. Patent Publication Nos. 2007-0191863 and 2009-0182421. These applications are incorporated by reference in their entirety.

Figure 2:
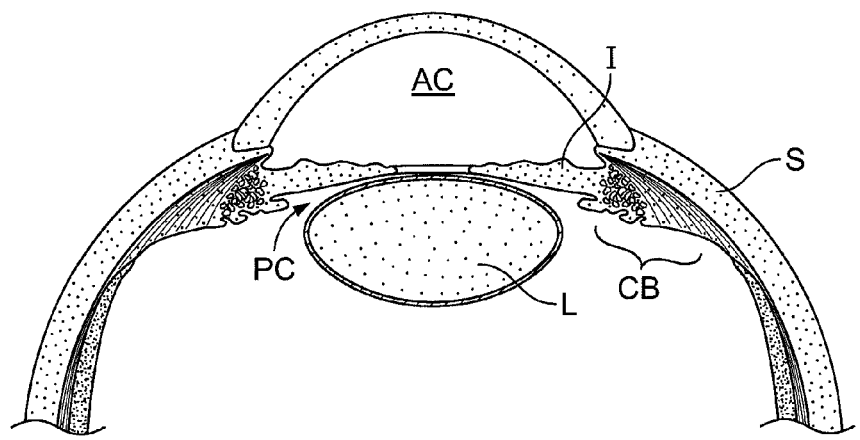
FIG. 2 is a cross-sectional view of a human eye.

FIG. 2 is a cross-sectional view of a portion of the human eye. The eye is generally spherical and is covered on the outside by the sclera S. The retina lines the inside posterior half of the eye. The retina registers the light and sends signals to the brain via the optic nerve. The bulk of the eye is filled and supported by the vitreous body, a clear, jelly-like substance. The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris I through which light passes. The volume between the iris I and the lens L is the posterior chamber PC. The volume between the iris I and the cornea is the anterior chamber AC. Both chambers are filled with a clear liquid known as aqueous humor.

The ciliary body CB continuously forms aqueous humor in the posterior chamber PC by secretion from the blood vessels. The aqueous humor flows around the lens L and iris I into the anterior chamber and exits the eye through the trabecular meshwork, a sieve-like structure situated at the corner of the iris I and the wall of the eye (the corner is known as the iridocorneal angle). Some of the aqueous humor filters through the trabecular meshwork near the iris root into Schlemm's canal, a small channel that drains into the ocular veins. A smaller portion rejoins the venous circulation after passing through the ciliary body and eventually through the sclera (the uveoscleral route).

Glaucoma is a disease wherein the aqueous humor builds up within the eye. In a healthy eye, the ciliary processes secrete aqueous humor, which then passes through the angle between the cornea and the iris. Glaucoma appears to be the result of clogging in the trabecular meshwork. The clogging can be caused by the exfoliation of cells or other debris. When the aqueous humor does not drain properly from the clogged meshwork, it builds up and causes increased pressure in the eye, particularly on the blood vessels that lead to the optic nerve. The high pressure on the blood vessels can result in death of retinal ganglion cells and eventual blindness.

Closed angle (acute) glaucoma can occur in people who were born with a narrow angle between the iris and the cornea (the anterior chamber angle). This is more common in people who are farsighted (they see objects in the distance better than those which are close up). The iris can slip forward and suddenly close off the exit of aqueous humor, and a sudden increase in pressure within the eye follows.

Open angle (chronic) glaucoma is by far the most common type of glaucoma. In open angle glaucoma, the iris does not block the drainage angle as it does in acute glaucoma. Instead, the fluid outlet channels within the wall of the eye gradually narrow with time. The disease usually affects both eyes, and over a period of years the consistently elevated pressure slowly damages the optic nerve.

The internal lumen of the implant 105 serves as a passageway for the flow of aqueous humor through the implant 105 directly from the anterior chamber to the suprachoroidal space. In addition, the internal lumen of the implant can be used as an access location to mount the implant 105 onto a delivery system, as described in more detail below. The internal lumen can also be used as a pathway for flowing fluid, such as an irrigation fluid or a visco-elastic substance(s), into the eye for flushing or to maintain pressure in the anterior chamber, or using the fluid to assist in dissection, visualization or hydraulic creation of a dissection plane into or within the suprachoroidal space. Fluid can be flowed into the suprachoroidal space, for example via a delivery cannula or through the internal lumen of the shunt. The fluid can be flowed into the eye with a pressure sufficient to form a dissection plane into or within the suprachoroidal space. The fluid can accumulate within the suprachoroidal space so as to form a lake. In general, hydro-dissection or the injection of fluids such as a visco-elastic substance(s) can be used to separate the ciliary body from the sclera to enlarge an area of detachment of the ciliary body from the sclera with or without insertion of a device.

Figure 3:
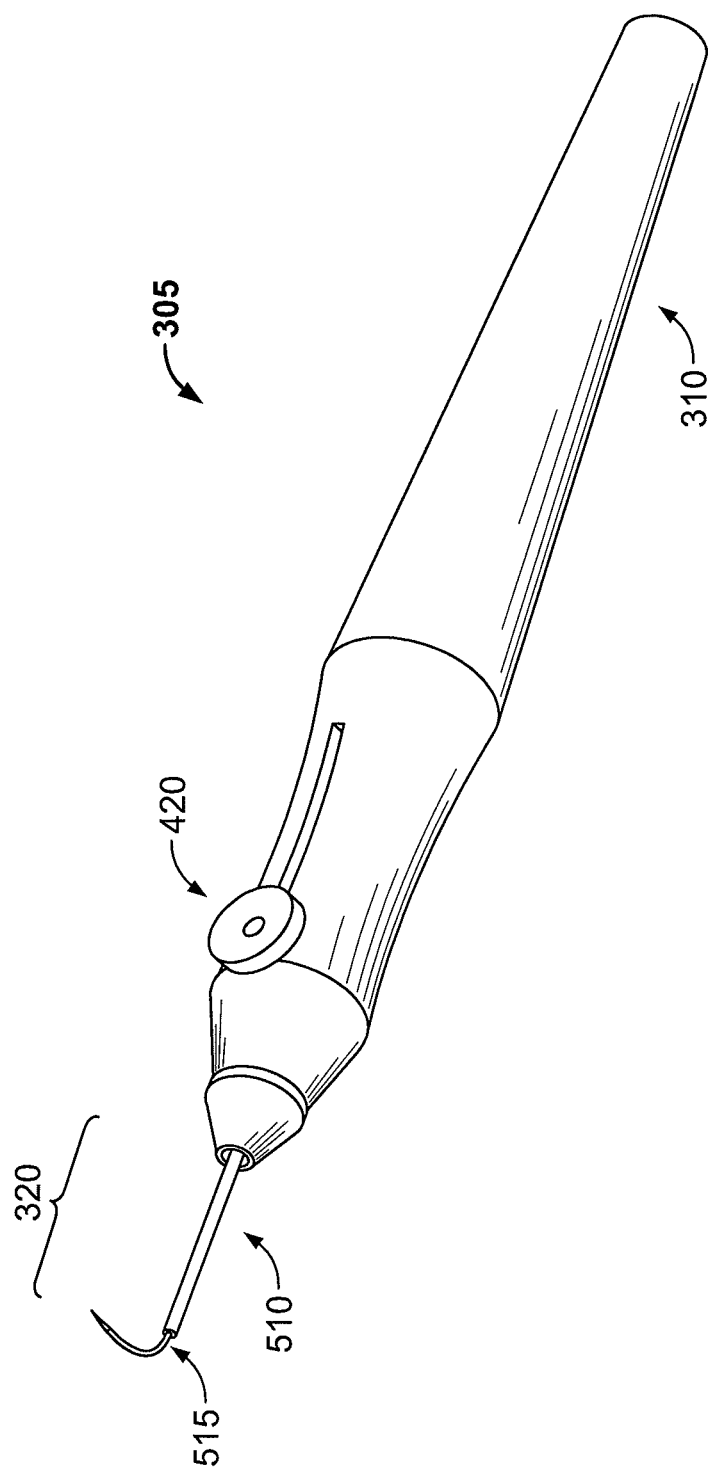
FIG. 3 shows an exemplary delivery system that can be used to deliver an implant into the eye.

In an embodiment, a delivery system is used to deliver an implant 105 into the eye, for example such that the implant 105 provides fluid communication between the anterior chamber and the suprachoroidal space. FIG. 3 shows an embodiment of a delivery system 305 that can be used to deliver the implant 105 into the eye. It should be appreciated that these delivery systems 305 are exemplary and that variations in the structure, shape and actuation of the delivery system 305 are possible.

The delivery system 305 generally includes a proximal handle component 310 and a distal delivery component 320. The proximal handle component 310 can include an actuator 420 to control the release of an implant from the delivery component 320 into the target location in the eye. The actuator 420 can vary in structure and mechanism and can include, for example, a button, switch, knob, slider, etc.

An embodiment of the delivery component 320 can include an elongate applier in the form of a guidewire 515 that inserts longitudinally through the internal lumen of the implant 105 and a "stopper" or sheath 510 positioned axially over the guidewire 515. The sheath 510 can aid in the release of the implant 105 from the delivery component 320 into the target location in the eye. The actuator 420 can be used to control the guidewire 515 and/or the sheath 510. For example, the sheath 510 can be fixed relative to the handle component 310 and act as a stopper that impedes the implant 105 from moving in a proximal direction as the guidewire 515 is withdrawn proximally from the implant 105 upon actuation of the actuator 420. In a first state, the guidewire 515 is extended distally relative to the sheath 510. Movement of the actuator 420, such as in the proximal direction, causes the guidewire 515 to slide proximally into the sheath 510. This effectively disengages the implant 105 off the distal end of the guidewire 515 and releases the implant 105 in a controlled fashion such that the target positioning of the implant 105 is maintained.

Figure 4E:
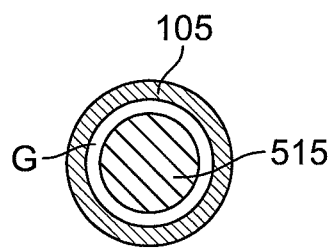
FIG. 4E is a cross-sectional view of an embodiment of a delivery system.
Figure 4F:
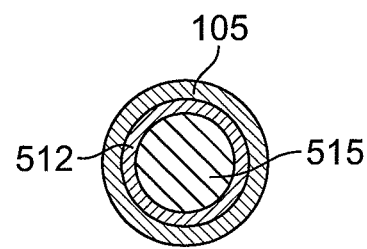
FIG. 4F is a cross-sectional view of the delivery system of FIG. 4A taken along line F-F.

As mentioned, the outer diameter of the guidewire 515 is generally smaller than the inner diameter of the implant 105 (i.e. the fluid channel) such that the implant 105 can be loaded onto the guidewire 515 by sliding the guidewire 515 into and through an internal lumen of the implant 105. In some instances, the outer diameter of the guidewire 515 can be significantly smaller than the internal diameter of the implant 105 thereby creating a gap G between the guidewire 515 and the implant 105 (see FIG. 4E). This gap G allows for the addition of an internal retention layer 512 or a retention coating to the delivery component 320 (see FIG. 4F) or the inner surface of the implant 105. The internal retention layer 512 can act to retain the implant 105 on the guidewire 515 during blunt dissection and implantation to prevent the implant 105 from inadvertently falling off the guidewire 515 until it is delivered to the desired target location within the eye. An advantage of an internal retention layer 512 is the very low profile of the delivery system 305 and a surgeon's improved ability to visualize each step of implantation.

FIGS. 4A-4D show cross-sectional schematic views of an implant 105 mounted on a delivery portion 320 for inserting the implant, for example from the anterior chamber into a region of the suprachoroidal space. The figures show an implant 105 mounted on the end of a guidewire 515, a sheath 510 sized and shaped to receive or abut a portion of the proximal end 125 of the implant 105, and a retention layer 512 providing an interference fit between the implant 105 and the guidewire 515. In this embodiment upon actuation the guidewire 515 slides in the proximal direction (arrow P) into the sheath 510. The proximal end 125 of the implant 105 abuts the distal edge of the sheath 510 to prevent the implant 105 from sliding in the proximal direction. This effectively disengages the implant 105 off the distal end of the guidewire 515 and controllably releases the implant 105 into the eye tissue. The retention layer 512 is shown coupled to and moving with the guidewire 515 such that the guidewire 515 and retention layer 512 are fully withdrawn into the sheath 510.

Figure 5:
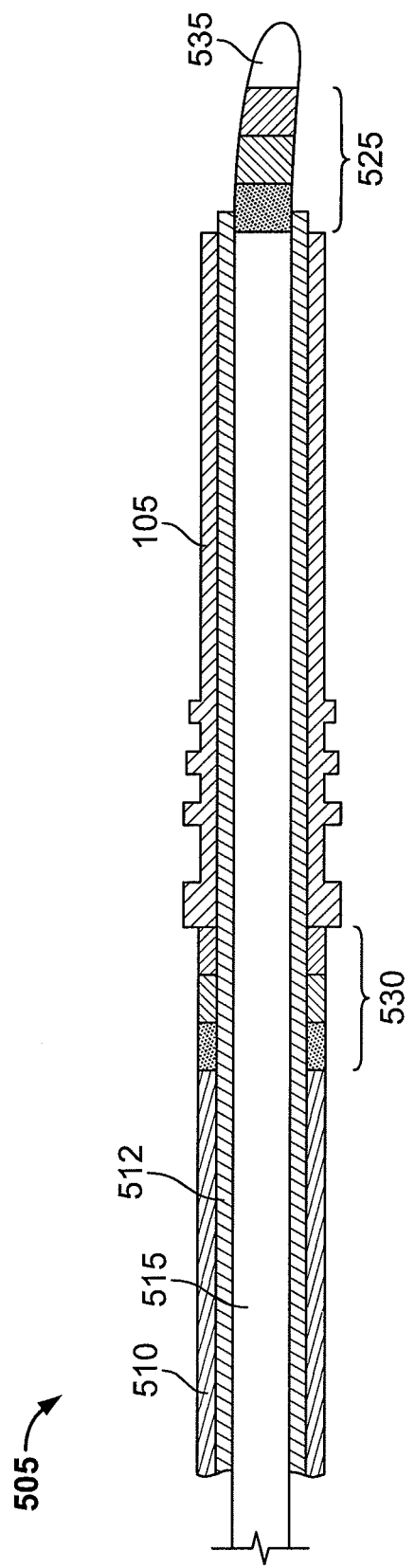
FIG. 5 shows a cross-sectional view of an embodiment of a delivery system including a graduated guidewire and sheath.

FIG. 5 shows a cross-sectional view of an implant 105 mounted on an embodiment of a delivery system 505 including a metering system to aid in obtaining the proper advancement depth of the implant 105 into a region of the eye, for example the suprachoroidal space, with minimal or no aid of a goniolens or imaging system. In this embodiment, the delivery system 505 includes a guidewire 515 having a metering system 525 located near its distal end. The guidewire 515 can be inserted through and surrounded by a sheath 510. In an embodiment, the sheath 510 also has a metering system 530 near its distal end. The metering systems 525, 530 can include one or more graduated markings. The configuration of the graduated markings can vary. For example, the graduated markings can be numbers, hatches, bands, patterns, color or other type of mark or combination of marks that can be observed by the surgeon with or without instrumentation during insertion of the implant 105 into eye tissues. It should be appreciated that the guidewire 515 metering system 525 can extend onto the retention layer 512 and/or the implant 105 itself.

It should also be appreciated that although a dual metering system is shown in the figures, a single meter can be used as well. In an embodiment a single metering system uses the limbus of the eye as a reference landmark in which the single meter is located on the sheath distal end. During delivery of the implant into the eye, once the single meter is no longer visible under the limbus, the implant is then released into the eye tissue. The final depth of placement of the implant can then be achieved using a goniolens. Alternately, the position of the implant can be left as-is as the marks on the sheath correlate to a predetermined depth for which the proximal region of the implant will protrude into the anterior chamber.

Although their configuration can vary, the graduated markings of each of the metering systems 525, 530 can correspond to one another. In addition, the distance between each of the corresponding graduated markings can correlate to the length of the implant. The correlation can take into account the length of the bands and the distance therebetween. The guidewire 515 metering system 525 can have visual, graduated markings of identical size, scale, spacing, color scheme, pattern and otherwise to the visual, graduated markings of the sheath 510 metering system 530. For example, the graduated markings can be bands of color. In an embodiment the metering systems 525, 530 can each be unique bands of color, for example, a ¼ mm band of red followed by ¼ mm band of yellow followed by ¼ mm band of green followed by ¼ mm band of orange etc.

In an embodiment, the metering systems 525, 530 can correspond and can be identical to one another. The guidewire 515 metering system 525 of this embodiment, however, is set back away from the distal-most tip of the guidewire 515 thereby creating an additional "blank" band 535. The width of the blank band 535 is pre-determined and corresponds to the desired width of the proximal end of the implant 105 that is to remain within the anterior chamber AC and outside of the tissue dissection region. The width of the blank band 535 need not be the same width as the other markings. In an embodiment, the width of the blank band 535 is 0.5 mm.

Figure 6A:
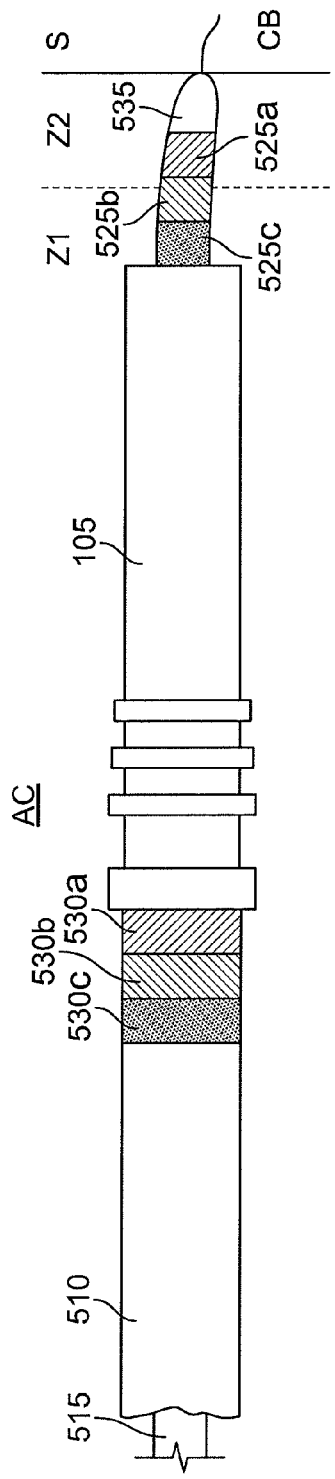
FIGS. 6A-6B show schematic views of an embodiment of a dual metering system for delivering an implant.
Figure 6B:
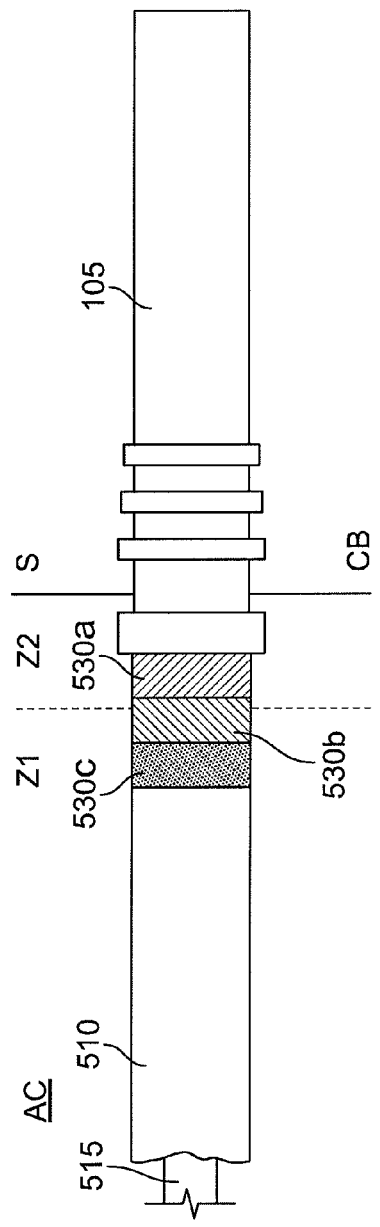

As best shown in FIGS. 6A-6B, a dual metering delivery system can be used to "blindly" insert an implant 105 to the desired depth into a region of the eye tissue. The term, "blind" is used to mean a goniolens or internal visualization system need not be used during delivery with such a system. The guidewire 515 and an implant 105 mounted thereon can be advanced through the anterior chamber AC and visualized directly by peering through the transparent cornea, indicated in the figure as viewing zone Z1. As shown in FIG. 6A, the guidewire 515 metering system 525 can include three bands, 525a, 525b and 525c and a distal-most blank band 535. Bands 525a, 525b, 525c can each be of a unique color, e.g., red, green and orange, respectively, or other type of unique marking. The sheath 510 metering system 530 can include a series of bands 530a, 530b and 530c that correspond to 525a, 525b and 525c, respectively. In this embodiment, the sheath 510 metering system 530 does not have a corresponding blank band.

In use the surgeon can advance the guidewire 515 a distance beyond viewing zone Z1 into the opaque portion of the cornea, or the "no see" zone Z2. The distal tip of the guidewire 515 can be gently inserted into the "no see" zone Z2 until resistance is felt to indicate the guidewire 515 is seated at a predetermined location, such as the scleral spur or the iris root part of the ciliary body, or another desired dissection point. At this point, the surgeon can read the band of the metering system 525 of the guidewire 515 that is visible in the viewing zone Z1 just adjacent to the "no see" zone Z2. For example, the surgeon can take a reading by observing the color band 525b (a green band, for example) near the junction of viewing zone Z1 and "no see" zone Z2. The surgeon can then advance the guidewire 515 with the implant 105 loaded thereon dissecting between the tissue layers of the ciliary body CB and the sclera S until the corresponding color band 530b on the sheath 510 is observed near the same junction of viewing zone Z1 and "no see" zone Z2. It should be appreciated that the metering systems can have additional markings or smaller gradations for desired precision and accuracy in implant positioning.

In an embodiment, the guidewire 515 metering system 525 includes a blank band 535 at its distal-most tip whereas the sheath 510 metering system 530 does not include a blank band. This results in a portion of the proximal end of the implant 105 remaining outside the tissue layers within the "no see" zone Z2 of the anterior chamber AC. This proximal portion of the implant 105 can have a width equal to the width of blank band 535. The dual metering systems 525, 530 with the additional blank band 535 at the distal tip of the guidewire 515 can provide an indirect measurement of implant position within the eye. A surgeon can advance the implant 105 to the proper depth and location between the tissue layers while maintaining a pre-defined proximal portion of the implant 105 remaining within the anterior chamber with minimal or no need for a goniolens or other visualization system.

FIG. 7A shows an exploded view of another embodiment of a delivery system that can be used to "blindly" insert an implant 105 to the desired depth and location, for example a region of the suprachoroidal space. The delivery system can include a guidewire 515 mounted on the upper surface of an elongate glide plate 705. The delivery system of FIG. 7A can also include a sheath or stopper. The glide plate can serve as part of the metering systems as well as a platform that can be used to move, protect, or deflect tissue during delivery of the implant into the eye. The guidewire 515 and/or sheath can have a metering system 545 along a region of its length as can the glide plate 705 (shown in the Figure as metering system 725). As in previous embodiments, the metering systems 725, 545 can include one or more graduated markings such as numbers, hatches, bands of color or other type of mark or combination of marks to be observed by the surgeon during insertion of the implant 105 into the eye tissues. The metering systems 725, 545 have marks of corresponding size, scale, spacing, color scheme, pattern and otherwise. The guidewire 515 and glide plate 705 metering systems 725, 545 can be aligned relative to each other such that upon advancing the guidewire 515 to align the corresponding visual marks of the metering systems 725, 545 the implant 105 is delivered to the target depth within a region of the suprachoroidal space and a region of the implant 105 remains outside of the eye tissue within the "no see" zone Z2 of the anterior chamber AC.

For example, FIGS. 7B-7C show top plan schematic views of the dual metering systems 725, 545 for delivering an implant 105 to the desired depth of a region of eye tissue, such as the suprachoroidal space. The glide plate 705 metering system 725 has a series of visual bands 725a, 725b, 725c, etc. as well as a blank band located at its distal-most tip. The series of visual bands 725a, 725b, 725c, etc. can each be of a unique color. The guidewire 515 metering system 545 has a series of visual bands 545a, 545b, 545c, etc. that correspond to the glide plate 705 visual bands 725a, 725b, 725c, etc. in size, shape, spacing, color or otherwise. The guidewire 515 with its metering system 545 is offset in a proximal direction from the glide plate 705 with its metering system 725 such that desired implantation depth is controlled by visually aligning the corresponding visual bands of each of the metering systems 725, 545 as the guidewire 515 is urged in a distal direction (arrow D). The blank band located at the distal-most tip of the glide plate 705 can allow for a corresponding region of the implant 105 to remain outside the eye tissue and within the "no see" zone Z2 of the anterior chamber AC. As with the previous embodiment, the delivery system can be used with minimal to no use of a goniolens or other visualization system. The guide plate 705 and guidewire 515 can be aligned prior to use. For example, the guide plate 705 and guidewire 515 can be offset by a predetermined amount of movement that the guide plate 705 can be moved proximally or a predetermined distance from the distal edge of the guide plate 705 and the distal tip of the guidewire 515.

In use for delivery of an implant into the suprachoroidal space S, the glide plate 705 and guidewire 515 can be advanced through the anterior chamber AC and can be visualized directly by peering through the transparent cornea, the viewing zone Z1. The surgeon can advance the glide plate 705 and guidewire 515 a distance beyond viewing zone Z1 into the opaque "no see" zone Z2. The delivery system can be advanced through Z2 until resistance is felt and the distal tip of the glide plate 705 abut tissue near the boundary of the iris root part of the ciliary body and the sclera. The broad surface area of the glide plate 705 allows a surgeon to gently push the iris down as the guidewire 515 and the implant 105 dissect and enter the tissues near the iris root portion of the ciliary body CB. The guide plate 705 can be made of a material that is configured to deflect in response to abutment with eye tissue when in the eye.

With the glide plate 705 seated at or around (e.g., above or below) the iris root and scleral spur part of the ciliary body CB, the surgeon can take a reading on the upper surface of the glide plate 705 by observing the visual band nearest the junction of the viewing zone Z1 and the "no see" zone Z2. The surgeon can then advance the guidewire 515 and sheath 510 (with the implant 105 loaded thereon in a distal direction (arrow D) such that the guidewire 515 and implant 105 dissect between the tissue layers of the sclera and the ciliary body CB. The guidewire 515 can be advanced until the corresponding guidewire 515 or sheath visual band (e.g. 545a) aligns with the glide plate 705 visual bands (e.g. 725a) on the glide plate 705 nearest the "no see" zone Z2 therein providing indirect measurement of the advancement of the implant 105 into the tissue.

The delivery devices described herein control the delivery depth of an implant. FIGS. 7D-7E illustrate an embodiment of a delivery system that includes a stop 750 mounted on the upper surface of the glide plate 705 and actuated into a stop position that prevents the implant 105 from moving proximally upon withdrawal of the guidewire when a sheath is not in use. As shown in FIGS. 7D-7E, the glide plate 705 and guidewire 515 are used as described above to deliver the implant 105 into a region of the suprachoroidal space S. The guidewire 515 can then be withdrawn in a proximal direction (arrow P) releasing the implant 105 in its target position. A stop 750 projecting from the upper surface of the glide plate 705 can abut against the proximal edge of the implant 105 and prevent the implant 105 from being withdrawn along with the guidewire 515.

In other embodiments, the metering system can employ illuminating light for visualization of graduated markings. For example, the graduated glide guidewire can include a series of graduated apertures such that backlighting the glide guidewire provides a visual indication of depth of implantation. The delivery systems described herein can also include imaging and illumination systems such as described in U.S. application Ser. No. 12/753,494, filed Apr. 2, 2010, which is incorporated herein by reference.

Methods of Implant Delivery

An exemplary method of delivering and implanting the implant into the eye is now described. In general, one or more implants 105 can be slideably loaded on a delivery system and implanted to a position that communicates with the suprachoroidal space as described herein. The loading of the implant on the guidewire of the delivery system can be aided by a retention layer (or a retention coating on the guidewire or the internal walls of the implant) that reversibly retains the implant on the tip of the guidewire while still maintaining a flexible and low profile guidewire. The loading of the implant 105 onto the delivery guidewire will be discussed in more detail below. The retention layer prevents the implant from falling off the guidewire inadvertently during delivery until the surgeon actuates the delivery component and effects controlled release of the implant from the guidewire 515, for example, upon proximal withdrawal of the guidewire 515. The implant 105 is then secured in the eye so that it provides fluid communication between the anterior chamber and the suprachoroidal space.

The guidewire 515 can be positioned on the delivery system such that the distal tip of the guidewire 515, the implant 105 and sheath 510 can penetrate through a small, corneal incision to access the anterior chamber, such as within the limbus of the cornea. In an embodiment, the incision is very close to the limbus, such as either at the level of the limbus or within 2 mm of the limbus in the clear cornea. The guidewire 515 can be used to make the incision or a separate cutting device can be used. For example, a knife-tipped device or diamond knife can be used to initially enter the cornea. A second device with a spatula tip can then be advanced over the knife tip wherein the plane of the spatula is positioned to coincide with the dissection plane.

The corneal incision has a size that is sufficient to permit passage of the implant on the guidewire, implant and sheath therethrough. In an embodiment, the incision is about 1 mm in size. In another embodiment, the incision is no greater than about 2.85 mm in size. In another embodiment, the incision is no greater than about 2.85 mm and is greater than about 1.5 mm. It has been observed that an incision of up to 2.85 mm is a self-sealing incision.

After insertion through the incision, the guidewire 515 is advanced into the anterior chamber along a pathway that enables the implant 105 to be delivered to a position such that the implant 105 provides a flow passageway from the anterior chamber AC to the suprachoroidal space. The guidewire 515 can be advanced further into the eye such that the blunt distal tip of the guidewire 515 and/or the implant 105 seats with and can penetrate the iris root IR or a region of the ciliary body CB or the iris root part of the ciliary body near its tissue border with the scleral spur SSp, to be discussed in more detail below.

The guidewire 515 can approach the iris root IR from the same side of the anterior chamber AC as the deployment location such that the guidewire 515 does not have to be advanced across the iris. Alternately, the guidewire 515 can approach the location from across the anterior chamber AC such that the guidewire 515 is advanced across the iris and/or the anterior chamber toward the opposite iris root. The guidewire 515 can approach the eye and the iris root IR along a variety of pathways. The guidewire 515 does not necessarily cross over the eye and does not intersect the optical axis of the eye. In other words, the corneal incision and the location where the implant is implanted at the iris root can be in the same quadrant (if the eye is viewed from the front and divided into four quadrants). Also, the pathway of the implant from the corneal incision to the iris root desirably does not pass through the optic axis of the eye to avoid interfering with the pupil.

Figure 8:
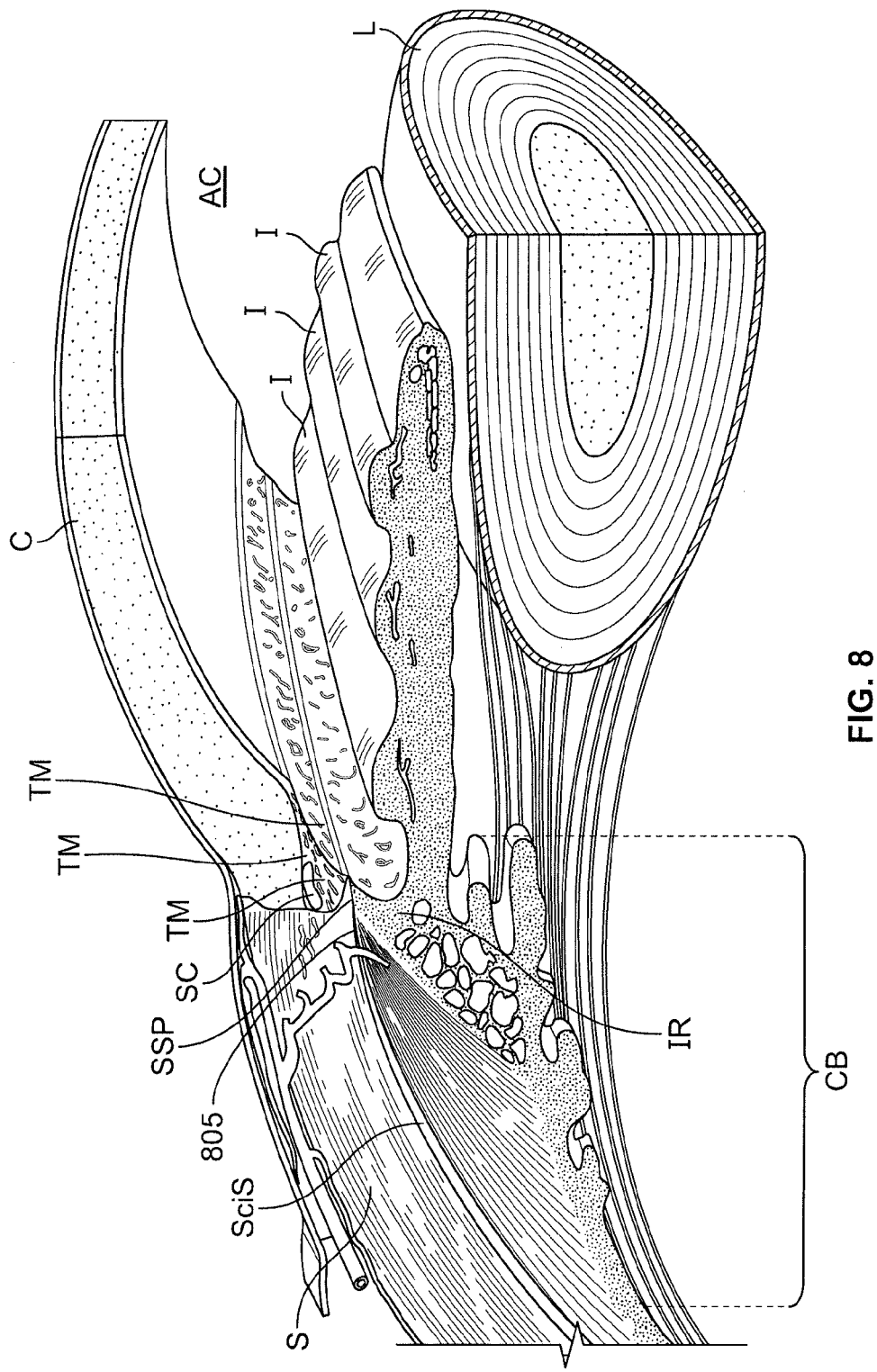
FIG. 8 shows an enlarged view of a portion of the anterior region of the eye in cross-section.

FIG. 8 shows an enlarged view of the anterior region of the eye showing the anterior chamber AC, the cornea C, the iris I, and the sclera S. The implant 105 mounted on the guidewire 515 can approach from the anterior chamber AC. They move along a pathway such that the dissection entry point of the distal tip of the guidewire 515 can penetrate the iris root IR near its junction with the scleral spur SSp or the iris root portion of the ciliary body CB or other desired location. The surgeon can rotate or reposition the handle of the delivery device in order to obtain a proper approach trajectory for the distal tip of the guidewire 515, as described in further detail below.

The guidewire 515 with the implant 105 positioned thereupon can be advanced from a region of the anterior chamber that can be viewed through the transparent zone of the cornea Z1 through to a region of the anterior chamber AC that is obscured by the opaque zone Z2 of the cornea C. The guidewire 515 and implant 105 can be advanced through Z2 of the cornea C until resistance is felt and the delivery device can be seated at a location near the iris root IR, the ciliary body or the iris root portion of the ciliary body. The surgeon then can take a reading by observing the visual mark on the guidewire 515 metering system 520 immediately adjacent to Z2 of the cornea C. The guidewire 515 can then be advanced further such that the guidewire 515 and implant 105 loaded thereon penetrate an area of fibrous attachment 805 between the scleral spur SSP and the ciliary body CB. This area of fibrous attachment 805 can be approximately 1 mm. Once the distal tip of the guidewire 515 penetrates and is urged past this fibrous attachment region 805, the guidewire 515 then more easily causes the sclera S to peel away or otherwise separate from the ciliary body CB and possibly the choroid as it follows the inner curve of the sclera S and enters the suprachoroidal space. A combination of the guidewire's tip shape, material, material properties, diameter, flexibility, compliance, coatings, pre-curvature etc. make it more inclined to follow an implantation pathway that mirrors the curvature of the inner wall of the sclera and between tissue layers such as between the sclera and the ciliary body, and between the sclera and the choroid.

The guidewire 515 can be continuously advanced into the eye in a distal direction until a corresponding visual mark on the sheath 510 metering system 530 is adjacent to Z2 of the cornea. This can result in the implant 105 reaching the desired depth of penetration while a proximal region of the implant 105 remains within the anterior chamber. The dissection plane of the guidewire 515 and implant 105 can follow the curve of the inner scleral wall such that the implant 105 mounted on the guidewire 515 after penetrating the iris root or the iris root portion of the ciliary body, bluntly dissects the boundary between tissue layers of the scleral spur SSp and the ciliary body CB such that a distal region of the implant extends into the suprachoroidal space. In an embodiment, the implant 105 is positioned such that it does not extend past the scleral spur SSP far enough to reach or otherwise contact the choroid. That is, the distal end of the implant does not reach and cannot contact the choroid. In another embodiment, the implant 105 extends sufficiently past the scleral spur SSP such that it is positioned between the tissue boundaries of the sclera and the choroid.

Figure 9:
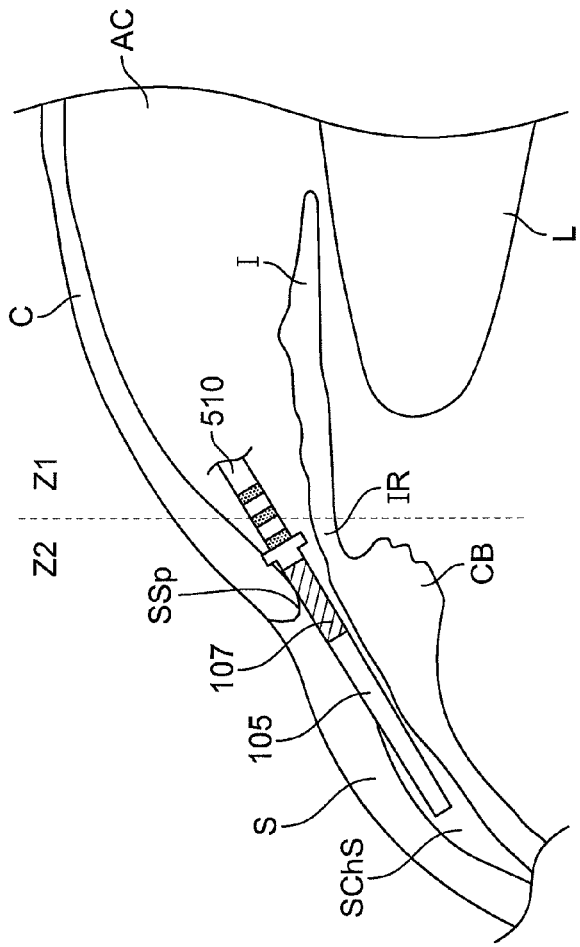
FIG. 9 shows an implant positioned within the eye and a graduated sheath.

FIG. 9 shows the implant 105 positioned within the suprachoroidal space SChS and abutting a sheath 510 having a metering system 530 thereon. A first portion of the implant 105 can be positioned within the suprachoroidal space SChS and a second portion of the implant 105 can remain within the anterior chamber AC. The width of the second portion of the implant 105 remaining within the anterior chamber AC can approximate the width of the blank band 535 of the guidewire 515, as described in more detail above. In one embodiment, at least 1 mm to 2 mm of the implant (along the length) remains in the anterior chamber AC. The implant 105 can be positioned so that a portion of the implant is sitting on top of the ciliary body CB. The ciliary body CB may act as a platform off of which the implant 105 can cantilever into the suprachoroidal space SChS. The implant 105 can lift or "tent" the sclera S outward such that the suprachoroidal space SchS is formed around the distal end of the implant 105. The tenting of the sclera S as shown in FIG. 9 has been exaggerated for clarity of illustration. It should be appreciated that the actual contour of the tented region of tissue may differ in the actual anatomy. The implant 105 can act as a flow pathway between the anterior chamber AC and the suprachoroidal space SchS without blockage of the outflow pathway by surrounding tissues such as the sclera or the choroid. In an embodiment the distal end of the implant 105 does not extend far enough to reach the choroid. In another embodiment, the distal end of the implant 105 reaches the choroid and may contact the choroid.

Once properly positioned, the implant 105 can then be released from the guidewire 515. The implant 105 can be released for example by withdrawing the guidewire 515 such that the implant 105 is effectively disengaged in a controlled manner from the tip of the guidewire 515 with the sheath 510 (for example via the manner described above with reference to FIGS. 4A-4D). A retention layer 512 can optionally be used to assist in retaining the implant 105 on the guidewire 515 during the steps of delivery. However, the relationship between the retention layer 512 and the implant 105 can be readily reversible such that the guidewire 515 and retention layer 512 can be withdrawn into the sheath 510 to controllably release the implant 105 from the tip of the guidewire upon arrival at the target location within the eye.

The implant 105 can include one or more structural features near its proximal region that aid to anchor or retain the implant 105 in the target region in the eye. The structural features can include flanges, protrusions, wings, tines, or prongs, and the like that can lodge into the surrounding eye anatomy to retain the implant 105 in place and prevent the implant 105 from moving further into the suprachoroidal space SchS. The structural features also provide regions for areas of fibrous attachment between the implant 105 and the surrounding eye anatomy. FIG. 9 illustrates schematically some structural features comprised of an approximately 1 mm circumferential band 107 of the implant 105 near the junction of the iris root and the scleral spur SSp along the inside of the scleral wall toward the back of the eye at which fibrous attachment can occur. Fibrous attachment can result, for example, from endothelial cell growth in, around and/or between retention features of the implant 105. In addition, a small amount of scarring in and around an area of fibrous tissue attachment between the scleral spur SSp and the ciliary body CB in the region of the iris root portion of the ciliary body can provide for additional fixation to prop up the implant in its target location.

Mounting Implant onto Delivery Device

The handling of and connection between the guidewire and the implant, which each have very small dimensions, can be challenging to the user. Further, because positioning of the implant onto the guidewire can affect the accuracy of the metering system loading the implant can be controlled using a loading device. Described below is a simple, quick and easy-to-use device for loading an implant onto a delivery device. The loading devices described herein can be used to securely hold and transport an implant, allow for easy handling by a user to properly align the implant relative to a delivery device. The loading device also reduces the likelihood of damaging either the implant or the guidewire during loading of the implant onto the delivery device.

Figure 10:
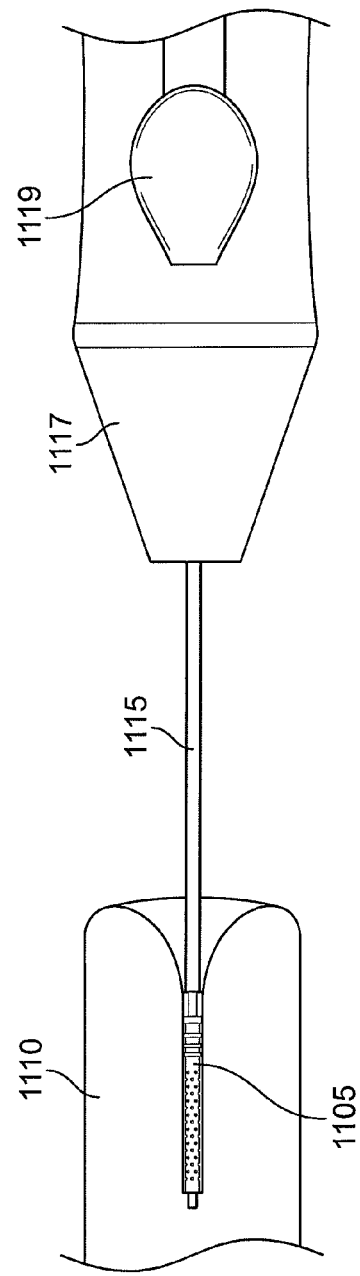
FIG. 10 shows a schematic, side view of a delivery device guidewire inserted through an implant positioned on the delivery device within an embodiment of a loading device.

FIG. 10 is a schematic, side view of a delivery device guidewire 1115 inserted through an implant 1105 positioned within a loading device 1110. Generally, a delivery device used to deliver an implant 1105 into the body includes a proximal handle component 1117 and a distal delivery component including a guidewire 1115. The proximal handle component 1117 can include an actuator 1119, such as a button, switch, knob, slider etc., to control the release of the implant 1105 from the guidewire 1115 once delivered to the target location in the body. The guidewire 1115 can have a cross-sectional size and shape that complements the cross-sectional size and shape of an internal lumen of the implant 1105 such that it can be inserted longitudinally therethough for delivery into the body. The outer diameter of the guidewire 1115 can be selected and optimized based on the material and flexibility of the material used for the guidewire 1115. In an embodiment, the outer diameter of the guidewire 1115 is between about 0.009" to about 0.013". The dimensions of the implant 1105 can vary as well. In an embodiment, the outer diameter of the implant 1105 is between about 0.016" to about 0.020" and an inner diameter of about 0.010" to about 0.015". The tiny dimensions of both the guidewire 1115 and the implant 1105, as well as the use of slippery, hydrophilic coatings on the guidewire 1115 to reduce friction during dissection, can cause handling difficulties by a user during loading of the implant onto a delivery device.

FIGS. 11A-11C illustrate an embodiment of a loading device 1110 generally includes a main body 1205 having a loading end 1207. The loading end 1207 of the main body 1205 includes an atraumatic or radial funnel 1215 that tapers into a cylindrical implant cavity holder 1220 and terminates at a relief 1225. The taper of the funnel 1215 guides a guidewire 1115 of a delivery device through the internal flow channel of the implant 1105 loaded within the implant cavity holder 1220. The relief 1225 allows for the tip of the guidewire 1115 to extend slightly beyond the implant 1105. The depth of the relief 1225 can accommodate the metering system 525 at the distal end of the guidewire 1115. The portion of the guidewire 1115 having the metering system 525 can extend into the relief 1225 such that the distal end of the implant 1105 is aligned with a selected mark on the metering system 525. The depth of the relief 1225 can also accommodate the additional "blank" band 535 of the metering system 525. A removable cap 1210 can be secured to the loading end 1207 of the main body 1205 such that inadvertent movement of an implant 1105 positioned within the implant cavity holder 1220 is prevented or controlled.

The implant cavity holder 1220 is shown in the figures as generally cylindrical, but the holder 1220 can also correspond in shape to the outer surface of the implant with which the loading device 1110 is to be used. The length of the implant cavity holder 1220 can vary such that the implant cavity holder 1220 can contain a plurality of implants 1105. For example, more than one implant 1105 can be positioned within the implant cavity holder 1220 such that they can simultaneously be loaded onto a single guidewire 1115 during a single insertion into the loading device 1110. Alternatively, the holder 1220 can be used to perform multiple loadings of the implant 1105 onto the guidewire 1115. The guidewire 1115 can be inserted into the implant cavity holder 1220 having a single implant 1105 positioned therein. The implant 1105 can be inserted or used and then the guidewire 1115 can be inserted back into the implant cavity holder 1220 having another implant 1105 positioned therein.

Although the implants described herein are shown as generally cylindrical, elongate elements having an internal flow channel running therethrough, the configuration of the implants can vary. For example, the internal flow channel of the implant can be used as an access location to mount the implant onto a guidewire 1115 of a delivery system as shown in FIG. 10. But it should be appreciated that the implant 1105 need not have a flow channel to be loaded onto a delivery device using the loading devices described herein. For example, the implant 1105 can be inserted longitudinally through an elongate channel of a delivery device (not shown) and the outer diameter of the implant captured by the delivery device.

As mentioned previously, the implants described herein can vary widely in shape, structure and also material. It should also be appreciated that other implantable devices can be loaded onto their respective delivery devices with the loader systems described herein. For example, the loading devices described herein can be used to load implants onto delivery devices for use in the lung, vascular, heart, spine and other regions of the body in which minimally-invasive methods are desirable.

FIGS. 12A-12C illustrate another embodiment of a loading device 1110 in which the main body 1205 incorporates ergonomic features. In this embodiment, the main body 1205 has an ergonomic shape, such as a funnel, trumpet, or other shape. The main body 1205 can also include outer, ergonomic finger guides 1325 and a cap 1210 also having an ergonomic shape.

FIGS. 13A-13B illustrate another embodiment of a loading device 1110 in which the protective cap 1210 is coupled to the main body 1205 such that a user can flip the cap 1210 off the loading end 1207 with a single motion of one hand. The cap 1210 can include a lip or flange 1230 that can be pressed by a user's thumb or finger to remove the cap 1210 from the loading end 1207 and reveal the tapered neck region of the loading device 1110 including the funnel 1215. The loading device 1110 described herein can incorporate features such that it can be used with a single hand.

Figure 14A:
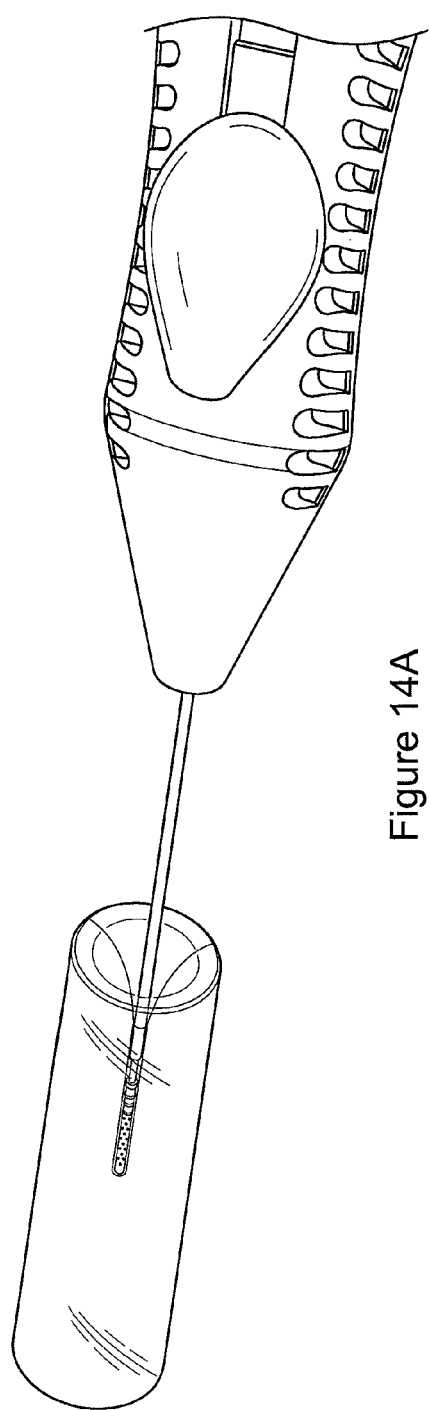
FIGS. 14A-14B illustrate another embodiment of a loading device manufactured of an optical clear finish.
Figure 14B:
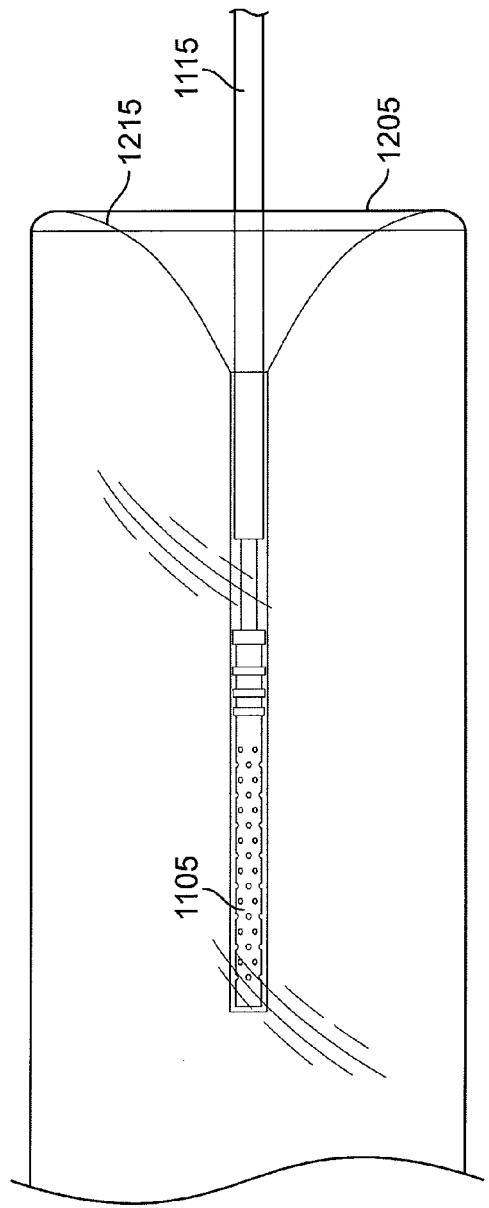

The main body 1205 of the loading device 1110 can be manufactured of a variety of materials including polymer, metal, ceramic, silicone and the like. As shown in FIGS. 14A-14B, the main body 1205 can have an optical clear finish such that the implant 1105 as well as a guidewire 1115 inserted through the funnel 1215 of the loading device 1110 can be visualized by the user. In an embodiment, the optical clear finish can include a lens system that magnifies the implant 1105 within the loading device 1110.

Figure 15A:
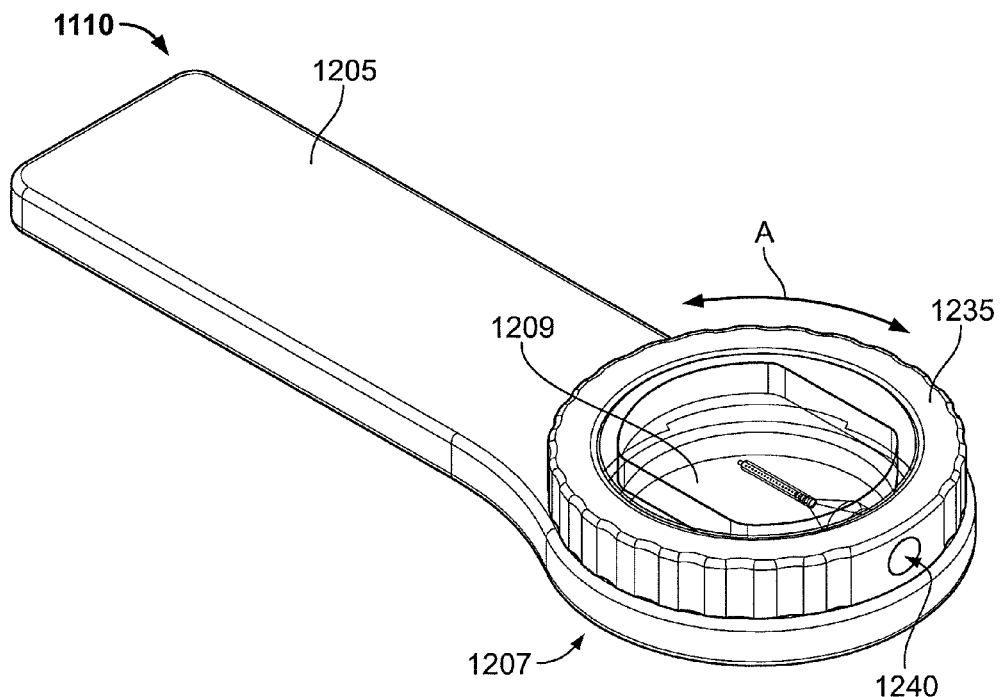
FIGS. 15A-15B illustrate another embodiment of a loading device.
Figure 15B:
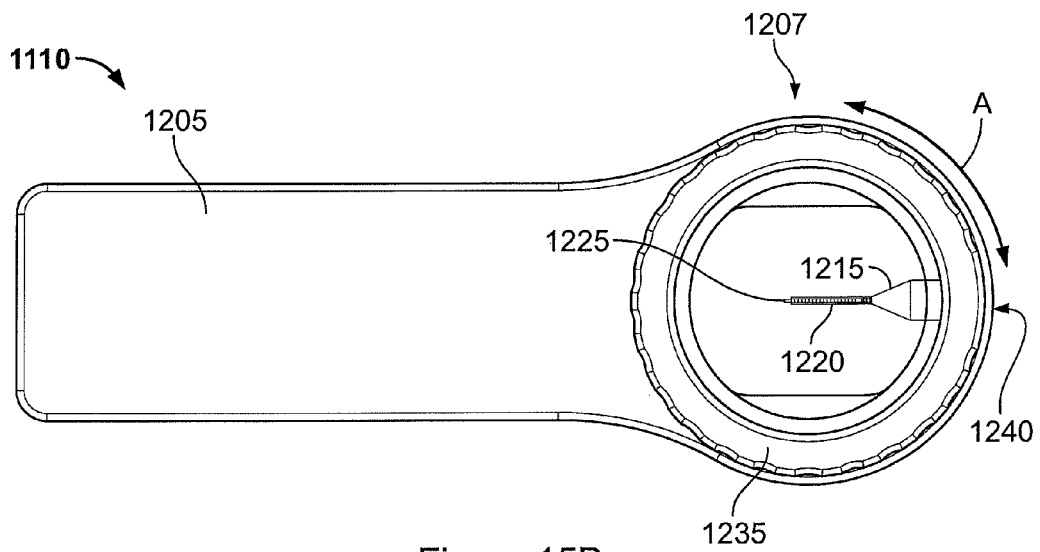

FIGS. 15A-15B illustrate another embodiment of a loading device 1110. In this embodiment, the loading device 1110 includes a main body 1205 and a loading end 1207 having a clear window with or without a magnifying lens 1209. As with other embodiments, the loading end 1207 can include an atraumatic funnel 1215 that tapers into an implant cavity holder 1220 and terminates at a relief 1225. In this embodiment, the loading device 1110 does not include a removable cap, but rather a rotatable outer ring 1235 having an access hole 1240 at a perimeter of the ring. Rotation of the outer ring 1235 along arrow A can align the access hole 1240 with an opening to the funnel 1215. Upon alignment with the opening to the funnel 1215, the access hole 1240 can be penetrated by the guidewire 1115.

Figure 16A:
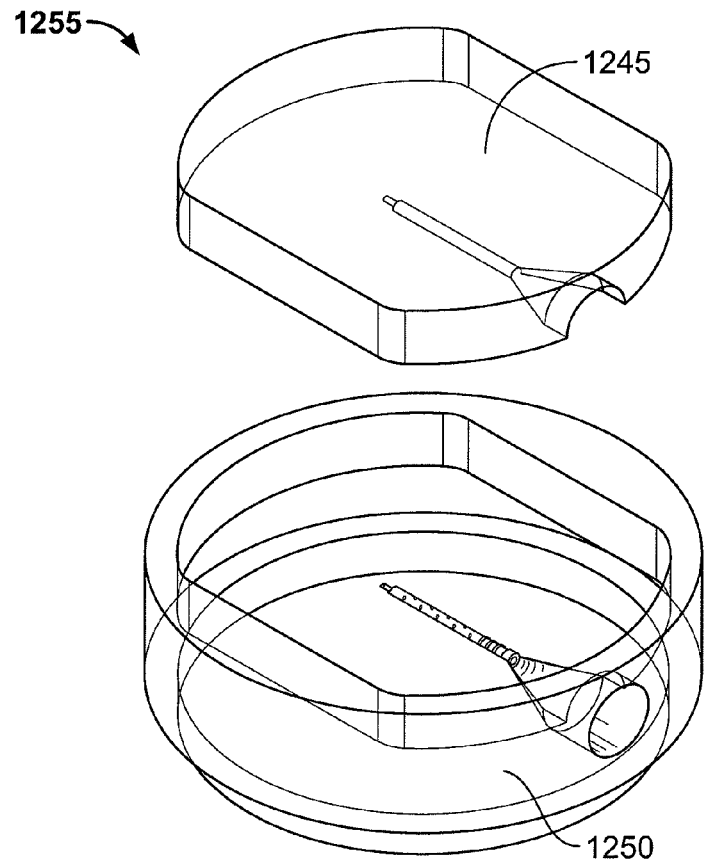
FIGS. 16A-16B illustrate a two-part loading end.
Figure 16B:
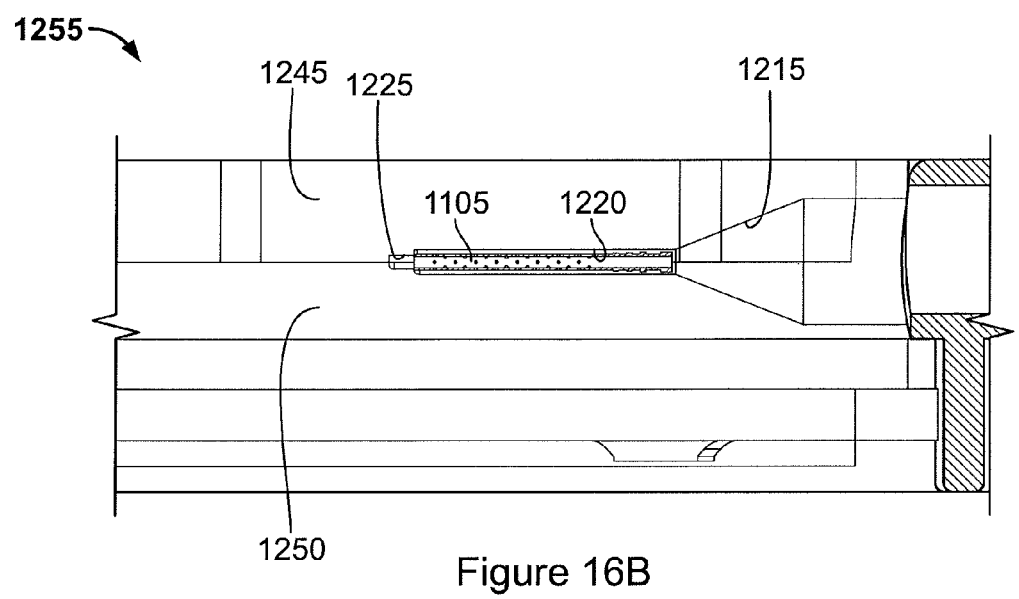

As shown in FIG. 16A-16B, the loading end 1207 can include a two-part "puck" 1255 around which the outer ring 1235 can rotate. The puck 1255 can include an upper portion 1245 and a lower portion 1250 each with corresponding wells such that when the upper and lower portions 1245, 1250 are coupled together they form the funnel 1215, implant cavity holder 1220 and relief 1225. This allows for the portion of the loading device 1110 that makes contact with the implant 1105 to be more easily cleaned.

During loading of an implant 1105 onto a guidewire 1115 of a delivery device, the implant 1105 is initially positioned within the implant cavity holder 1220 of the loading device 1110. One or more implants 1105 can come preloaded in the loading device 1110 and packaged in a sterile, disposable accessory kit. Upon removal from the packaging, the cap 1210 can be removed from the loading device 1110 to reveal the tapered neck region of the funnel 1215. Alternatively, the outer ring 1235 can be rotated such that the access hole 1240 aligns with the opening of the tapered neck region of the funnel 1215. A detent or other mechanism can be used such that the user is able to sense when the loader is in the open and closed positions. Ratchets, clicks or visual alignment system can also be used. The guidewire 1115 of the delivery device is inserted through the funnel 1215 and through the internal lumen of the implant 1105. A hard stop can be felt as the guidewire 1115 enters the relief 1225. The inner lumen of the implant 1105 is sufficiently smooth relative to the guidewire 1115 to permit the implant 1105 to easily slide over the guidewire 1115. As the guidewire 1115 is withdrawn from the funnel 1215 the implant 1105 remains coupled to the distal end of the guidewire 1115. The guidewire 1115 can have a retention coating such that the inner diameter of the implant 1105 can be gripped by the guidewire. Alternatively, the retention coating can be on the inner diameter of the implant 1105. The friction fit between the guidewire 1115 and the inner diameter of the implant allows for the implant 1105 to be withdrawn from the loader. The retention layer also prevents the implant 1105 from being inadvertently knocked off the guidewire 1115 or from affecting the alignment between a metering system at the distal end of the guidewire 1115 and the implant.

The implant 1105 can be placed into the funnel 1115 of the loading device 1110 at the time of manufacture and before the loading device 1110 is packaged and sterilized. The implant 1105 can be secured inside of the loading device 1110 by the cap 1210 or rotatable outer ring 1235 that traps the implant 1105 inside the loading device 1110. In the case of a shape-changing implant, the implant 1105 can be loaded with a tool that compresses the implant 1105 into a configuration that can be positioned inside the loading device 1110. The tool can then release the implant 1105 trapping it inside of the loading device 1110.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A method of using a delivery system for implantation of a device into an eye in the absence of a lens or other imaging system, the method comprising:

mounting an implant on a delivery device comprising a guidewire having a sheath coupled to the guidewire, wherein the guidewire comprises a first metering system at a distal end of the guidewire and the sheath comprises a second metering system at a distal end of the sheath, the first and second metering systems having corresponding graduated markings;
inserting the implant on the delivery device into an anterior chamber through an incision in a cornea;
advancing the implant on the delivery device through a transparent zone of the anterior chamber toward an opaque zone of the anterior chamber;
seating a distal end of the guidewire at eye tissue where resistance is felt;
reading through the transparent zone a first graduated marking of the first metering system, wherein the first graduated marking is aligned with an edge between the transparent zone and the opaque zone;
advancing the implant on the guidewire into the eye tissue beyond where resistance is felt; and
reading through the transparent zone a second graduated marking on the second metering system, wherein the second graduated marking is aligned with the edge between the transparent zone and the opaque zone.

2. The method of claim 1, further comprising releasing the implant from the guidewire.

3. The method of claim 2, wherein the implant provides a flow passageway between the anterior chamber and the suprachoroidal space.

4. The method of claim 1, wherein inserting the implant comprises inserting the entire implant into the anterior chamber.

5. The method of claim 1, wherein the first metering system further comprising a blank band at the distal end region of the guidewire having a width.

6. The method of claim 5, wherein the width of the blank band corresponds to a width of the implant remaining within the anterior chamber once the implant is inserted into the eye tissue.

7. The method of claim 1, further comprising retaining the implant on the guidewire using a polymeric retention coating.

8. The method of claim 1, wherein seating a distal end of the guidewire at eye tissue where resistance is felt comprises seating the guidewire with a portion of the ciliary body having a tissue border with the scleral spur.

9. The method of claim 1, wherein advancing the implant on the guidewire into the eye tissue beyond where resistance is felt comprises positioning a distal end of the implant at least partially between a portion of the ciliary body and a portion of the sclera within a supraciliary space.

10. The method of claim 1, wherein advancing the implant on the guidewire into the eye tissue beyond where resistance is felt comprises positioning a distal end of the implant at least partially between a portion of the choroid and a portion of the sclera within a suprachoroidal space.

* * * * *